United States Patent [19]

Karrer et al.

[11] 4,002,768
[45] Jan. 11, 1977

[54] NEW PHENYLALKINYL ETHERS

[75] Inventors: Friedrich Karrer, Basel; Saleem Farooq, Aesch, both of Switzerland

[73] Assignee: CIBA-GEIGY Corporation, Ardsley, N.Y.

[22] Filed: June 27, 1975

[21] Appl. No.: 590,761

[30] Foreign Application Priority Data

July 3, 1974 Switzerland .................. 9133/74
June 4, 1975 Switzerland .................. 7215/75

[52] U.S. Cl. .................. 424/337; 260/609 F
[51] Int. Cl.² .................. C07C 149/32
[58] Field of Search .................. 260/609 F; 424/337

[56] References Cited

UNITED STATES PATENTS

| 3,155,733 | 11/1964 | Reifschneider | 260/609 F |
| 3,268,592 | 8/1966 | Sterling | 260/609 F |
| 3,718,686 | 2/1973 | Chodnekar et al. | 260/609 F |

FOREIGN PATENTS OR APPLICATIONS 667,891   4/1966   Belgium .................. 260/609 F

*Primary Examiner*—Lewis Gotts
*Assistant Examiner*—D. R. Phillips
*Attorney, Agent, or Firm*—Harry Falber

[57] ABSTRACT

Phenylalkinyl ethers of the formula

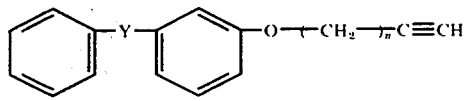

wherein $n$ is an integer from 1 to 3 and Y represents oxygen or sulphur, a process for their manufacture, a pesticidal composition containing them and a method of controlling pests are described.

3 Claims, No Drawings

PHENYLALKINYL ETHERS

The present invention provides phenylalkinyl ethers, a process for their manufacture and a method of using them in pest control.

The phenylalkinyl ethers have the formula

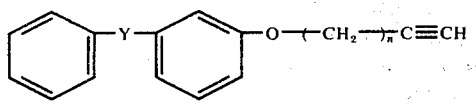
(I)

wherein $n$ is an integer from 1 to 3 and Y represents oxygen or sulphur.

Preferred compounds on account of their action are those of the formula I wherein $n$ is 1 or 3 and Y represents oxygen or sulphur.

The compounds of the formula I are manufactured by methods which are known per se, for example as follows:

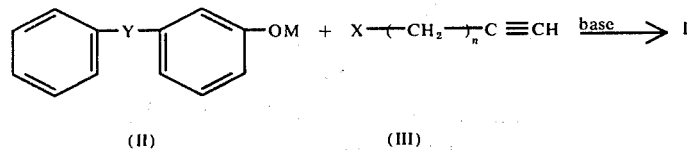

In the above formulae II and III, $n$ and Y have the meanings assigned to them in formula I, X represents a halogen atom, especially chlorine or bromine, and M is a metal of the 1st. or 2nd. main group of the Periodic Table, in particular sodium, potassium or calcium.

Examples of suitable bases are tertiary amines, such as trialkylamines, pyridine, dialkyl anilines; also organic bases, such as hydrides, hydroxides, alkoxides and carbonates of alkali metals and alkaline earth metals. The process is normally carried out at a reaction temperature between 0° and 150° C preferably between 0° and 80° C, at normal pressure and in the presence of inert solvents or diluents.

Examples of suitable solvents or diluents are: ethers, e.g. diethyl ether, diisopropyl ether, 1,2-dimethoxyethane, dioxan, tetrahydrofuran, N,N-dialkylated carboxamides, such as dimethyl formamide; ketones, e.g. acetone, methyl ethyl ketone or cyclohexanone; and also hexamethylphosphoric triamide, dimethyl sulphoxide or alcohols of 2 to 5 carbon atoms, e.g. isopropanol.

The starting materials of the formulae II and III are known compounds or compounds which can be manufactured in a manner analogous to known methods described in the literature.

Compounds of the formula I are suitable for combating a variety of animal and plant pests, especially insects and acarides. A number of compounds of the formula I also act as synergists in insecticides and acaricides. They are especially suitable for combating insects of the families: acrididae, blattidae, gryllidae, gryllotalpidae, tettigoniidae, cimicidae, pyrrhocoridae, reduviidae, aphidae, delphacidae, dispididae, pseudococcidae, chrysomelidae, coccinellidae, bruchidae, scarabaeidae, dermestidae, tenebrionidae, bostrichidae, cucujidae, curculionidae, tineidae, noctuidae, lymantridae, pyralidae, galleridae, culicidae, tipulidae, stomoxydae, muscidae, calliphoridae, trypetidae and pulicidae, as well as acarides of the families: ixodidae, argasidae, tetranychidae, dermanyssidae.

The insecticidal or acaricidal action can be substantially broadened and adapted to given circumstances by addition of other insecticides and/or acaricides. Examples of suitable additives are: organic phosphorus compounds, nitrophenols and derivatives, formamidines, ureas, carbamates, chlorinated hydrocarbons, or pyethroids.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, stickers, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology.

The compositions according to the invention are manufactured in known manner by intimately mixing and/or grinding active substances of the formula I with the suitable carriers, optionally with the addition of dispersants or solvents which are inert to the active substances.

The active substances may take, and be used in, the following forms:
Solid forms:
Dusts, tracking agents, granules, coated granules, impregnated granules and homogeneous granules.
Liquid forms:
a. active substances which are dispersible in water: wettable powders, pastes, emulsions;
b. solutions.

The content of active substance in the above described compositions is between 0.1% to 95%.

The active substances of the formula I can, for example, be formulated as follows:

Dusts

The following substances are used to manufacture (a) a 5% and (b) a 2% dust:

(a).

5 parts of active substance
95 parts of talcum (b).

2 parts of active substance
1 part of highly disperse silicic acid
97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:

(a).

40 parts of active substance,
5 parts of sodium lignin sulphonate,
1 part of sodium dibutyl-naphthalene sulphonate,
54 parts of silicic acid.

(b).

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

(c).

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselgur
46 parts of kaolin.

(d).

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10%, (b) a 25% and (c) a 50% emulsifiable concentrate:

(a).

10 parts of active substance,
3.4 parts of epoxidised vegetable oil,
13.4 parts of a combination emulsifier consisting of fatty alcohol polyglycol ether and alkyl aryl sulphonate calcium salt,
40 parts of dimethylformamide,
43.2 parts of xylene, (b).

25 parts of active substance,
2.5 parts of epoxidised vegetable oil,
10 parts of an alkylarylsulphonate/fatty alcohol-glycol ether mixture,
5 parts of dimethylformamide,
57.5 parts of xylene.

(c).

50 parts of active substance,
4.2 parts of tributylphenol polyglycol ether,
5.8 parts of calcium dodecylbenzenesulphonate,
20 parts of cyclohexanone,
20 parts of xylene.

From these concentrates it is possible to produce by dilution with water, emulsions of any desired concentration.

Spray

The following constituents are used to prepared (a) a 5% and (b) a 95% spray:

(a)

5 parts of active substance,
1 part of epichlorohydrin,
94 parts of benzene (boiling limits 160° C–190° C).

(b)

95 parts of active substance,
5 parts of epichlorohydrin.

EXAMPLE 1

Manufacture of 1-propargyloxy-3-phenyl-mercapto-benzene 10.8 g (0.078 mole) of finely powdered anhydrous potassium carbonate are added to a solution of 15.2 g (0.075 mole) of 3-hydroxydiphenylsulphide in 80 ml of anhydrous acetone and the mixture is boiled for 1 hour. Then 9.5 g (0.08 mole) of propargyl bromide are added dropwise within 15 minutes and the batch is boiled for a further 4 hours at reflux temperature. The reaction solution is worked up by filtering off precipitated matter and removing the solvent from the precipitate in vacuo. The residue is dissolved in ether and the solution is washed 3 times with 10% potassium hydroxide solution and then 4 times with saturated saline solution. The ethereal phase is dried over sodium sulphate and the solvent is then distilled off in vacuo to yield the compound of the formula

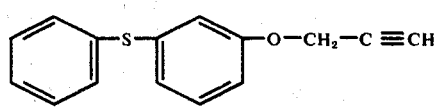

as an oil with a refractive index of $n_D^{20}$: 1.6219.

The following compounds can also be manufactured in analogous manner:

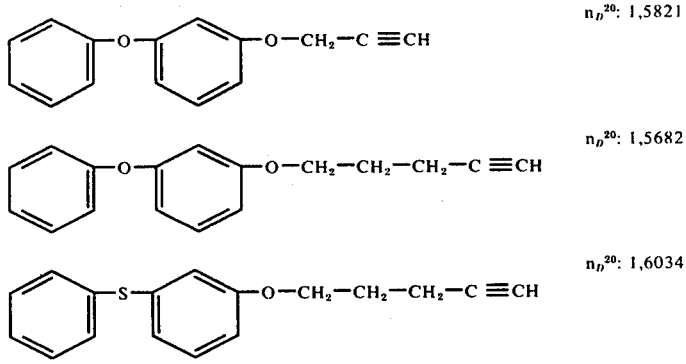

$n_D^{20}$: 1,5821

$n_D^{20}$: 1,5682

$n_D^{20}$: 1,6034

EXAMPLE 2

Insecticidal action against *musca domestica*

A given amount of a solution of the active substance in acetone (concentration of active substance = 0.05%) was pipetted onto 50 g of maggot substrate in beakers. After the treated substrate had been thoroughly mixed, the acetone was allowed to evaporated off for at least 20 hours.

25 1 day-old maggots were then put into each beaker. After 5 days the pupae were flushed out and deposited in the same beaker. Mortality was determined after 10 days. In this test the compounds according to Example 1 acted well against *musca domestica*.

EXAMPLE 3

Insecticidal action against aedes aegypti

Amounts of a 0.1% solution of active substance in acetone are pipetted onto the surface of 150 ml of water in beakers to give concentrations of 10,5 and 1 ppm respectively. After evaporation of the acetone, 30–40 2 day-old aedes larvae are put into the beakers. Mortality is determined after 1, 2 and 5 days.

The compounds of Example 1 acted well in this test against *aedes aegypti*.

EXAMPLE 4

Insecticidal action against *spodoptera littoralis*

15 cm high cotton plants were sprayed with 25 ml of a solution (acetone/water 1:1) containing 0.1% of active substance. After the solution had dried, each plant was populated with 5 spodoptera caterpillars (3rd. stage). A plastic cylinder was then slipped over the plant and sealed with a copper gauze cover. The mortality was determined after 2 days. In this test the compounds according to Example 1 exhibited good action against *spodoptera littoralis*.

EXAMPLE 5

Insecticidal action against *leptinotarsa decemlineata*

15 cm high potato plants were sprayed with a solution (acetone/water 1:1) containing 0.05% of active substance. After the solution had dried, each plant was populated with 10 *leptinotarsa larvae* (3rd. stage). A plastic cylinder was slipped over the plant and sealed with a copper gauze cover.

The mortality was determinated after 2 days. In this test the compounds according to Example 1 exhibit good action against *leptinotarsa decemlineata*.

EXAMPLE 6

Action against spider mitos

*Phaseolus vulgaris* (dwarf beans) had an infested piece of leaf from a mass culture of *tetranychus urticae* placed on them 12 hours before the test for the acaricidal action. The mobile stages which have migrated to the plants were sprayed with the emulsified test preparations from a chromatography atomiser so that the sprayed preparation did not run off. The number of living and dead larvae, adults and eggs were evaluated after 2 to 7 days under a stereoscopic microscope and the result expressed in percentages. During the intervening period, the treated plants were kept in greenhouse compartments at 25° C. The compounds according to Example 1 were active in the above test against eggs, larvae and adults of *tetranychus urticae*.

We claim:
1. The compound of the formula

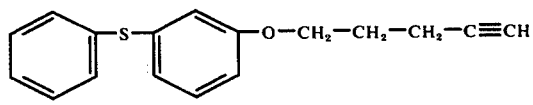

2. An insecticidal and acaricidal composition comprising an insecticidally and acaricidally effective amount of a compound of the formula of claim 1 together with a suitable inert carrier therefor.

3. A method for combatting insects and acarids which comprises applying thereto or to the locus thereof an insecticidally and acaricidally effective amount of a compound of the formula of claim 1.

* * * * *